(12) United States Patent
Tam et al.

(10) Patent No.: US 9,394,519 B2
(45) Date of Patent: Jul. 19, 2016

(54) METHODS TO PRODUCE MAST CELL CULTURE

(71) Applicant: Apollonian Biosystems Limited, Palo Alto, CA (US)

(72) Inventors: See-Ying Tam, Palo Alto, CA (US); Yee San Issan Tam, Hong Kong (HK); Hang Yung Alaster Lau, Hong Kong (HK)

(73) Assignee: Apollonian Biosystems Limited, Palo Alto, CA (US)

( * ) Notice: Subject to any disclaimer, the term of this patent is extended or adjusted under 35 U.S.C. 154(b) by 348 days.

(21) Appl. No.: 14/243,900

(22) Filed: Apr. 3, 2014

(65) Prior Publication Data

US 2014/0212971 A1 Jul. 31, 2014

Related U.S. Application Data

(62) Division of application No. 13/596,048, filed on Aug. 28, 2012, now abandoned.

(60) Provisional application No. 61/529,247, filed on Aug. 31, 2011.

(51) Int. Cl.
*C12N 5/02* (2006.01)
*C12N 5/0787* (2010.01)

(52) U.S. Cl.
CPC .......... *C12N 5/0642* (2013.01); *C12N 2500/02* (2013.01); *C12N 2501/125* (2013.01); *C12N 2501/2304* (2013.01); *C12N 2501/2306* (2013.01); *C12N 2501/2309* (2013.01)

(58) Field of Classification Search
CPC ................. C12N 2501/2309; C12N 2501/125; C12N 2501/2304; C12N 2501/2306
See application file for complete search history.

(56) References Cited

U.S. PATENT DOCUMENTS

2011/0015400 A1   1/2011   Graf et al.

OTHER PUBLICATIONS

Lappalainen et al., A protocol for generating high numbers of mature and functional human mast cells from peripheral blood, Clinical and Experimental Allergy, 2007, 37:1404-1414.
Wang et al., Buffy coat preparation is a convenient source of progenitors for culturing mature human mast cells, Journal of Immunological Methods, 2006, 309:69-74.
Rafei et al., A CCL2-based fusokine as a novel biopharmaceutical for the treatment of CCR-2-driven autoimmune diseases, Critical Reviews in Immunology, 2010, 30(5):449-461.
Wang, et al., Functional characterization of human mast cells cultured from adult peripheral blood, International Immunopharmacology, 2006, 6:839-847.
Andersen, et al., Comparison of short term in vitro cultured human mast cells from different progenitors-peripheral blood-derived progenitors generate highly mature and functional mast cells, Journal of Immunological Methods, 2008, 336:166-174.

*Primary Examiner* — Prema Mertz
(74) *Attorney, Agent, or Firm* — Eagle IP Limited; Jacqueline C. Lui

(57) ABSTRACT

The present invention relates to mast cell cultures that are derived from hematopoietic progenitors and the use thereof. The invention describes a method for generating in-vitro cultures of human mast cells with functional phenotype of connective tissue-type mast cells. By monitoring the levels of chemokines released into the medium, such mast cell cultures can be used as a cell-based assay to assess regulation of mast cell functions and pharmacological activities of tryptase inhibitors.

10 Claims, 9 Drawing Sheets

*: Toll-like receptor ligands; : Secretagogues; *: Ionophores

*: Toll-like receptor ligands; : Secretagogues; *: Ionophores

METHODS TO PRODUCE MAST CELL CULTURE

CROSS REFERENCES TO RELATED APPLICATIONS

The application is a divisional of the U.S. Non-provisional application Ser. No. 13/596,048, filed on Aug. 28, 2012, which claims priority to and the benefit of U.S. Provisional Application Ser. No. 61/529,247, filed on Aug. 31, 2011, which are hereby incorporated by reference.

FIELD OF INVENTION

The present invention relates to cell culture of mast cells derived from hematopoietic progenitors and the use thereof. In particular, the present invention relates to in-vitro human mast cell cultures with functional phenotype of connective tissue-type mast cells.

BACKGROUND OF INVENTION

Mast cells are immune cells that are derived from hematopoietic progenitors from the bone marrow and mature in peripheral tissues. Mast cells are major effector cells of many allergic and inflammatory reactions and express high-affinity receptors for immunoglobulin E (IgE). Crosslinking of IgE receptors with IgE and specific antigen initiates mast cell activation, leading to the release of a wide spectrum of mediators such as histamine, lipid mediators, and many cytokines and chemokines. In rodents, two types of mast cells have been identified based on their phenotypic characteristics: connective tissue-type and mucosal-type. These two populations of mast cells differ in location, cell size, staining properties, ultrastructure, mediator content, and T-cell dependency. Human mast cells are distinguished on the basis of their protease composition. Human $MC_{TC}$ mast cells contain both tryptase and chymase in their granules and exhibit functional characteristics similar to those of connective tissue-type mast cells. $MC_{TC}$ mast cells are found predominantly in the skin and intestinal submucosa. Human $MC_T$ mast cells, on the other hand, contain only tryptase and exhibit functional characteristics similar to those of mucosal-type mast cells. $MC_T$ mast cells are predominant in the alveolar wall and gastric mucosa.

A protocol for generating mature human mucosal-type like mast cells ($MC_T$) from CD34$^+$ progenitors isolated from peripheral blood of human adult donors was published in 2006 (Wang et al. 2006. *Journal of Immunological Methods*, 309:69-74.). In 2007, Lappalainen et al. reported a method for generating mature human connective tissue-type like mast cells ($MC_{TC}$) from human peripheral blood (Lappalainen et al. 2007. *Clinical and Experimental Allergy*, 37:1404-1414). Specifically, in the method described by Lappalainen et al., a time period of nine weeks is required to generate fully mature and functional human connective tissue-type like mast cells.

SUMMARY OF INVENTION

It is an object of the present invention to provide an alternate method to generate in-vitro cultures of mature human mast cells from hematopoietic progenitors.

Accordingly, the present invention, in one aspect, provides a mast cell culture product made by a process comprising (a) treating CD34$^+$ progenitor cells under hypoxic condition in a medium comprising stem cell factor (SCF), interleukin-6 (IL-6) and interleukin-3 (IL-3) to generate an initial-stage cell culture; (b) treating the initial-stage cells under hypoxic condition in a medium comprising SCF, IL-6 and interleukin-9 (IL-9) to form an intermediate-stage cell culture; and (c) treating the intermediate-stage cells under normoxic condition in a medium comprising SCF and IL-6 to generate an immature mast cell culture.

In one embodiment, the immature mast cell is further treated in step (d), comprising treating the immature mast cells under normoxic condition in a medium comprising SCF, IL-6 and interleukin-4 (IL-4), thereby generating a mature mast cell culture.

In one embodiment, the CD34$^+$ progenitor cells are derived from human.

In one embodiment of the present invention, the CD34$^+$ progenitor cells are treated under hypoxic condition for about 1 week in step (a).

In one embodiment of the present invention, the initial-stage cell culture is treated under hypoxic condition for 0.5-2.5 weeks in step (b).

In another embodiment of the present invention, the initial-stage cell culture is treated under hypoxic condition for 0.5-1.5 weeks in step (b).

In another embodiment of the present invention, the initial-stage cell culture is treated under hypoxic condition for 1 week in step (b).

In one embodiment, the intermediate-stage cell culture is treated under normoxic condition for 2.5-3.5 weeks in step (c).

In another embodiment, the intermediate-stage cell culture is treated under normoxic condition for 3 weeks in step (c).

In one embodiment, the immature mast cell culture is treated under normoxic condition for about 1 week in step (d).

In one embodiment, the concentration of IL-3 in the medium in step (a) is 0.1-4 ng/ml. In yet another embodiment, the concentration of IL-3 in the medium in step (a) is 0.5-2 ng/ml; in a further embodiment, the concentration of IL-3 in the medium in step (a) is 1 ng/ml.

In one embodiment, the concentration of IL-6 in the media in steps (a), (b), (c) and (d) is 50-500 ng/ml. In yet another embodiment, the concentration of IL-6 in the media in steps (a), (b), (c) and (d) is 80-200 ng/ml; in a further embodiment, the concentration of IL-6 in the media in steps (a), (b), (c) and (d) is 100 ng/ml.

In one embodiment, the concentration of SCF in the media in steps (a), (b), (c) and (d) is 100-500 ng/ml. In yet another embodiment, the concentration of SCF in the media in steps (a), (b), (c) and (d) is 150-300 ng/ml; in a further embodiment, the concentration of SCF in the media in steps (a), (b), (c) and (d) is 200 ng/ml.

In another embodiment, the concentration of IL-9 in the medium in step (b) is 1-50 ng/ml. In a further embodiment, the concentration of IL-9 in the medium in step (b) is 15 ng/ml.

In one embodiment, the concentration of IL-4 in the medium in step (d) is 1-100 ng/ml. In a further embodiment, the concentration of IL-4 in the medium in step (d) is 10 ng/ml.

In another aspect, the present invention provides a method of culturing mast cells comprising the steps of (a) treating CD34$^+$ progenitor cells under hypoxic condition for about 1 week in a medium comprising SCF, IL-6 and IL-3 to generate an initial-stage cell culture; (b) treating the initial-stage cell culture under hypoxic condition for about 0.5-2.5 weeks in a medium comprising SCF, IL-9 and IL-6 to form an intermediate-stage cell culture; (c) treating the intermediate-stage cell culture under normoxic condition for 2.5-3.5 weeks in a medium comprising SCF and IL-6 to generate an immature mast cell culture.

In one implementation of the present invention, the method of culturing mast cell further comprises the step of (d) treating the immature mast cell under normoxic condition for about 1 week in a medium comprising SCF, IL-6 and IL-4.

In one embodiment, the CD34$^+$ progenitor cells are derived from human.

In another implementation of the present invention, the initial-stage cell culture is treated under hypoxic condition for 0.5-1.5 weeks in step (b).

In another implementation of the present invention, the initial-stage cell culture is treated under hypoxic condition for 1 week in step (b).

In another implementation, the intermediate-stage cell culture is treated under normoxic condition for 3 weeks in step (c).

In one implementation, the concentration of IL-3 in the medium in step (a) is 0.1-4 ng/ml. In yet another implementation, the concentration of IL-3 in the medium in step (a) is 0.5-2 ng/ml; in a further implementation, the concentration of IL-3 in the medium in step (a) is 1 ng/ml.

In one implementation, the concentration of IL-6 in the media in steps (a), (b), (c) and (d) is 50-500 ng/ml. In yet another implementation, the concentration of IL-6 in the media in steps (a), (b), (c) and (d) is 80-200 ng/ml; in a further implementation, the concentration of IL-6 in the media in steps (a), (b), (c) and (d) is 100 ng/ml.

In one implementation, the concentration of SCF in the media in steps (a), (b), (c) and (d) is 100-500 ng/ml. In yet another implementation, the concentration of SCF in the media in steps (a), (b), (c) and (d) is 150-300 ng/ml; in a further implementation, the concentration of SCF in the media in steps (a), (b), (c) and (d) is 200 ng/ml.

In another implementation, the concentration of IL-9 in the medium in step (b) is 1-50 ng/ml. In a further implementation, the concentration of IL-9 in the medium in step (b) is 15 ng/ml.

In one implementation, the concentration of IL-4 in the medium in step (d) is 1-100 ng/ml. In a further implementation, the concentration of IL-4 in the medium in step (d) is 10 ng/ml.

In a further aspect, the present invention provides a method of assessing regulation of mast cell functions by measuring the level of monocyte chemoattractant protein 1 (MCP-1) (also known as chemokine ligand 2, (CCL2)) wherein the MCP-1 is secreted by mast cells over a period of time in a subject.

In one implementation, the regulation is a dysregulation of mast cell functions related to an inflammation-related condition, a disease or a disorder in a subject.

In one implementation, the mast cells are sensitized by immunoglobulin E (IgE) and then stimulated by anti-IgE. In another implementation, the mast cells are incubated with interferon-γ and then stimulated by aggregated immunoglobulin G$_1$ (IgG$_1$).

In another implementation, the level of MCP-1 is measured over 6-22 hours after stimulation.

In another aspect, the present invention provides a method of assessing tryptase-inhibitory activity of an agent comprising the steps of (a) stimulating mast cells in the presence of the agent and; (b) measuring the level of MCP-1 secreted by mast cells over a period of time.

In one implementation, the mast cells are induced to secrete tryptase by treatment with anti-IgE. In another embodiment, human IgE is used together with its antibody, anti-IgE, to activate the mast cells to secrete MCP-1. In another implementation, the mast cells are induced to secrete tryptase by treatment with aggregated IgG$_1$. In another embodiment, interferon-γ is used together with aggregated IgG$_1$ to activate the mast cells to secrete MCP-1.

In another implementation, the level of MCP-1 is measured over 6-22 hours.

In another aspect, the present invention provides a cell culture of functionally mature human mast cells derived from progenitor cells expressing the CD34 antigen comprising a homogenous population of human mast cells showing phenotypic and functional maturity at the sixth week in culture.

In one embodiment, the cells of the cell culture express both chymase and tryptase In one embodiment, the cells of the cell culture exhibit functional activation in response to stimulation by compound 48/80 or ionophores In another embodiment, the cells of the cell culture exhibit functional activation in response to activation of cell surface receptors on the cells. In one embodiment the cell surface receptors are selected from high-affinity IgE receptors, high-affinity IgG receptors, Toll-like receptors and Substance P receptors.

There is a distinct advantage to the present invention. The present invention provides a shorter protocol with time period of less than nine weeks for generating human connective tissue-type like mast cells from human buffy coats. These mast cells can reach phenotypic and functional maturity in a shorter period (6 weeks) than those generated by using previously published protocols.

DETAILED DESCRIPTION OF THE PREFERRED EMBODIMENTS

Figure 1:
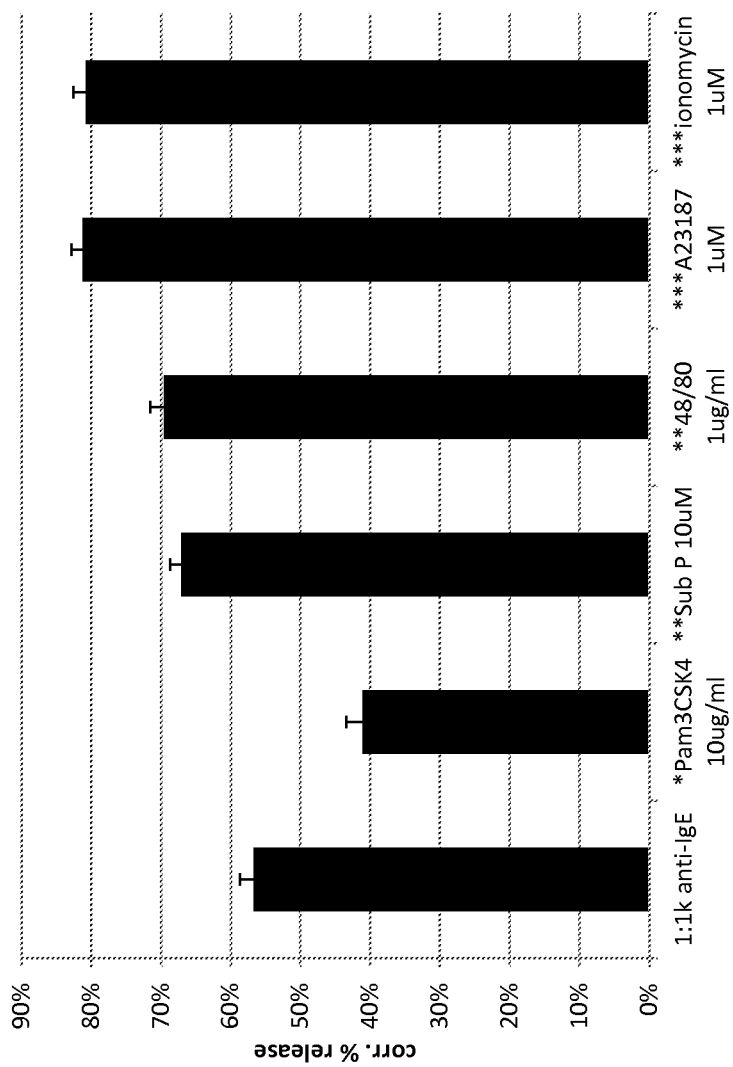
FIG. 1 shows histamine release by human mast cells in response to different stimuli according to one embodiment of the present invention.
Figure 2:
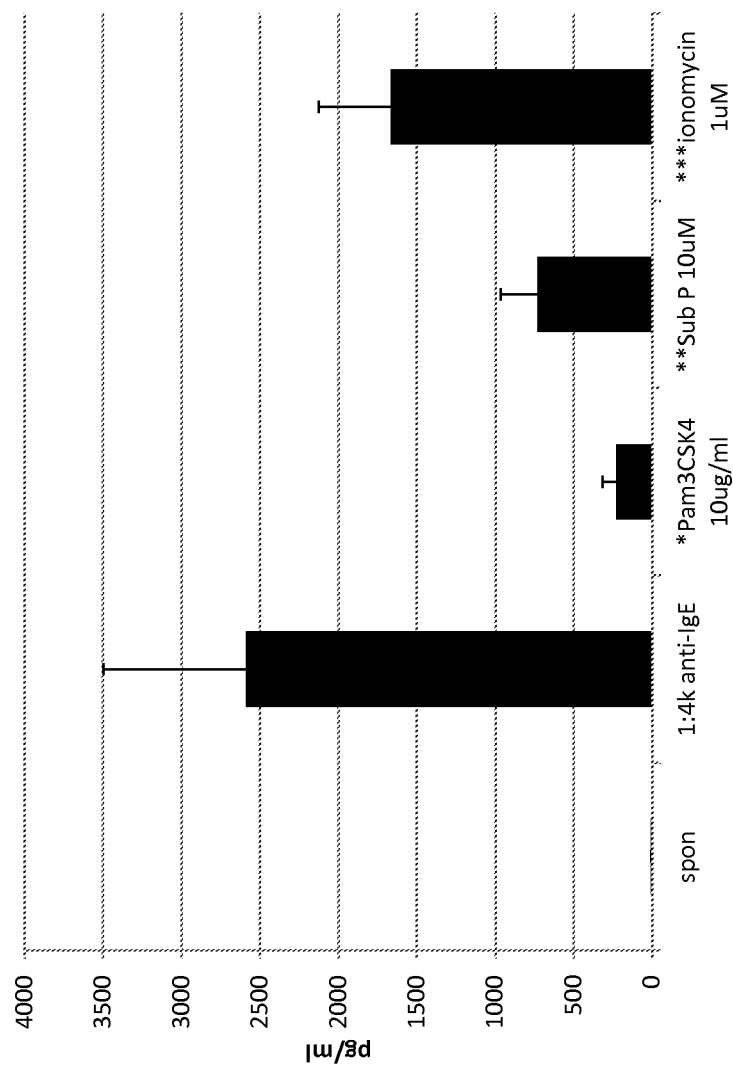
FIG. 2 shows PGD$_2$ release by human mast cells in response to different stimuli according to one embodiment of the present invention.
Figure 3:
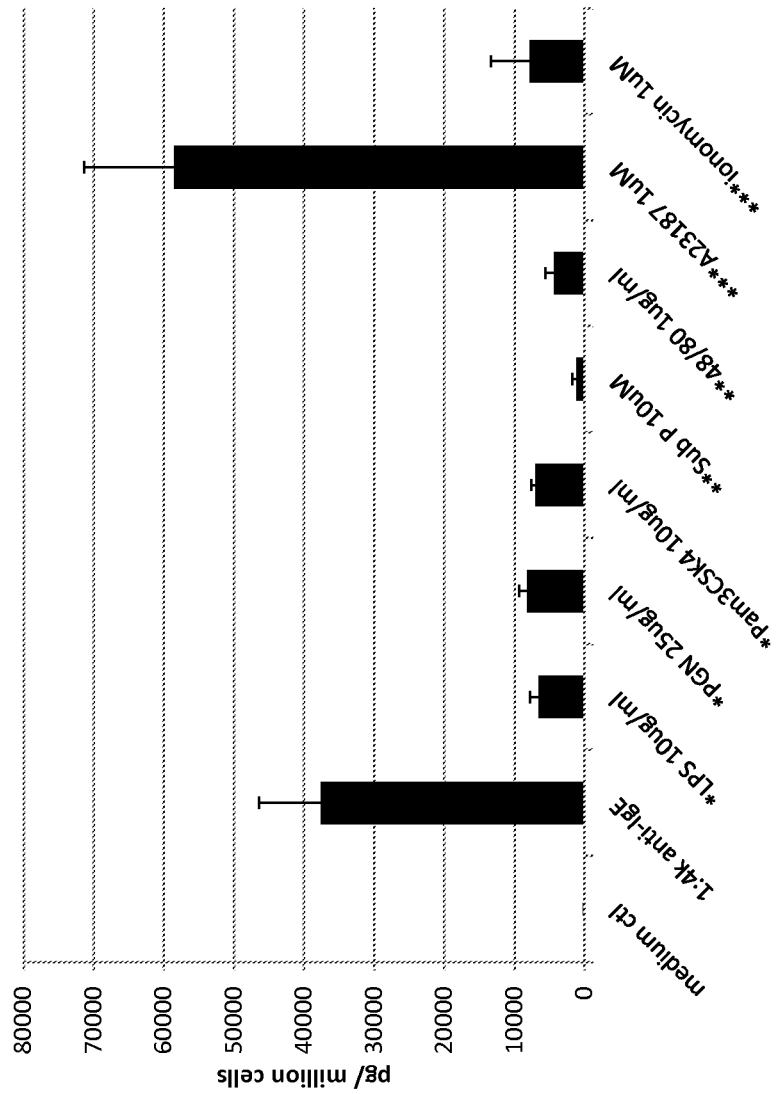
FIG. 3 shows IL-8 release by human mast cells in response to different stimuli according to one embodiment of the present invention.
Figure 4:
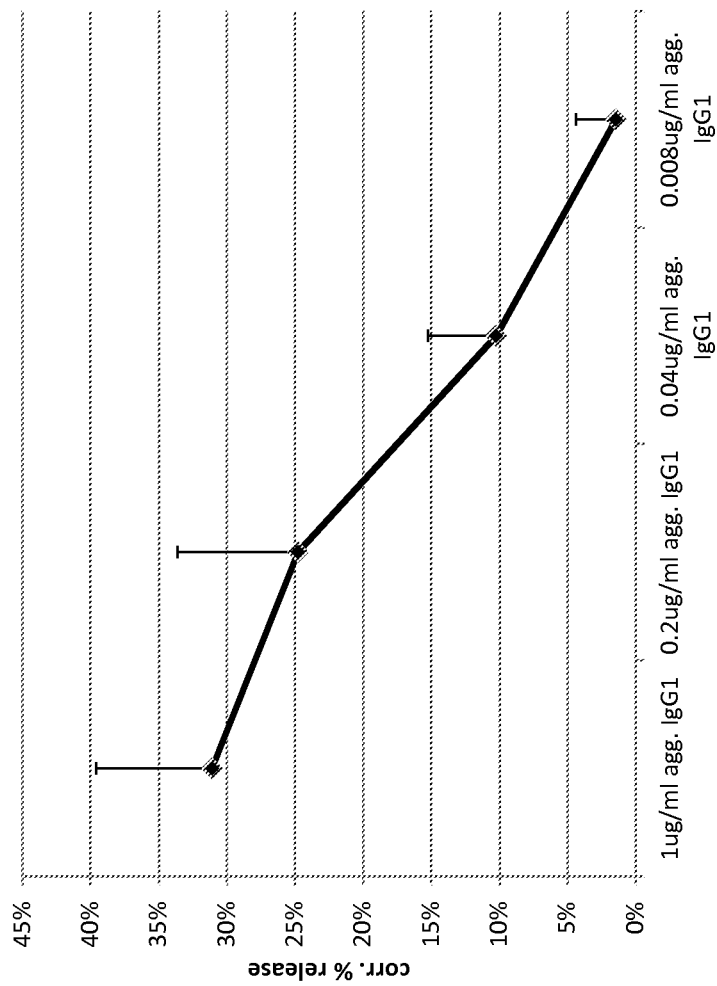
FIG. 4 shows histamine release by IFN-γ-pretreated human mast cell in response to aggregated IgG$_1$ according to one embodiment of the present invention.

It is to be understood that the invention is not limited to the particular methodologies, protocols, cells, assays, and reagents described herein, as the following are examples only and the conditions may vary. It is also to be understood that the terminology used herein is intended to describe particular embodiments of the present invention, and is in no way intended to limit the scope of the present invention as set forth in the appended claims.

It must be noted that as used herein and in the appended claims, the singular form "a", "an", and "the" include plural references unless context clearly dictates otherwise. Thus, for example, a reference to "an agent" includes a plurality of such agents.

Unless defined otherwise, all technical and scientific terms used herein have the same meanings as commonly understood by one of ordinary skill in the art to which this invention belongs.

Although any methods and materials similar or equivalent to those described herein can be used in the practice or testing of the present invention, the preferred methods, devices, and materials are now described. All publications cited herein are incorporated herein by reference in their entireties for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, genetics, immunology and pharmacology, within the skill of the art.

The term "a week" refers to a period of time of more than 145 hours and less than 191 hours.

As used herein and in the claims, "CD34+ progenitor cell" means progenitor cell expressing the CD34 antigen.

The term "subject" is used herein in its broadest sense. Subjects may include isolated cells, either prokaryotic or eukaryotic, or tissues grown in culture. In certain embodiments, a subject is an animal, particularly an animal selected from a mammalian species including rat, rabbit, bovine, ovine, porcine, canine, feline, murine, equine, and primate, particularly human.

As used herein and in the claims, "comprising" means including the following elements but not excluding others.

Example 1

Generation of Human Mast Cells with Functional Phenotype of Connective Tissue-Type Mast Cells 1a. Isolation of CD34+ Progenitor Cells from Pripheral Blood Buffy Coat (PBBC)

Fresh buffy coat of healthy adult donors was obtained from blood transfusion center in Hong Kong. Mononuclear cells were separated from PBBC using Ficoll-Paque Plus (GE Medical System) according to manufacturer's instructions. Briefly, 15 ml of PBBC was diluted with 15 ml PBS and layered gently on top of 15 ml Ficoll-Paque Plus. After centrifugation at 400×g for 30 min at room temperature (without brake), mononuclear cells were collected at the interface and washed with PBS. Residual red blood cells were lysed by incubating the cells in haemolytic buffer ($NH_4Cl$, $KHCO_3$, 235 $EDTA_2Na$) at room temperature for 3 min. Cell lysis was then terminated by addition of an equal volume of MACS buffer (PBS with 0.5% BSA and citrate-dextrose solution). The cells were then centrifuged, washed and resuspended in MACS buffer. CD34+ progenitors were isolated from the mononuclear cell suspension using MACS system (Miltenyi Biotec) according to the manufacturer's instructions. Briefly, the mononuclear cells were counted with heamatocytometer. Around $1 \times 10^9$ cells were incubated with Fc blocker+CD34 antibody attached MACS beads at 4° C. for 30 min. Unbound MACS beads were removed by washing with MACS buffer. The cell suspension was then loaded into a magnetic separation column. The CD34+ cells retained in the magnetic column were then eluted after removing the column from the magnetic field. The CD34+ progenitors were then washed with PBS, counted again, and resuspended in a density of $5 \times 10^5$ cells/ml in complete IMDM (Iscove's Modified Dulbecco's Medium, insulin-transferrin-selenium, penicillin-streptomycin, 2-mercaptoethanol, BSA).

1b. Culturing Conditions for Human Mast Cells

The CD34+ progenitors were seeded in 6-well plates in a density of $5 \times 10^5$ cells/ml. At the day of isolation, cells were cultured in complete IMDM with 200 ng/ml SCF, 100 ng/ml IL-6 and 1 ng/ml IL-3. After one week, spent medium was replaced by complete IMDM with 200 ng/ml SCF, 100 ng/ml IL-6 and 15 ng/ml IL-9. For week 2 to week 4, the cells were cultured in complete IMDM with 200 ng/ml SCF and 100 ng/ml IL-6. At week 5, the medium was replaced by complete IMDM with 200 ng/ml SCF, 100 ng/ml IL-6 and 10 ng/ml IL-4. At week 6, the human mast cell culture was ready for sensitization with IgE followed by activation by anti-IgE. After week 6, medium was replaced by complete IMDM with 100 ng/ml SCF and 50 ng/ml IL-6 on a weekly basis. The mast cell culture remained functionally responsive for at least 20 weeks.

For the first 2 weeks the culture was kept in a hypoxic incubator set at 37° C., 5% $O_2$ and 5% $CO_2$. Afterwards, the culture was transferred to a normoxic incubator set at 37° C., 21% $O_2$ and 5% $CO_2$.

Table 1 below illustrates the flow-chart of the above 6-week protocol for culturing human connective tissue-type like mast cells from human buffy coats. Under this protocol of the present invention, a shorter time is required for the mast cells to reach phenotypic and functional maturity than that using the protocol described by Lappalainen et al. Using a concentration of 1 ng/ml, instead of 5 ng/ml as used by Lappalainen et al., for IL-3, a higher percentage of the CD34+ progenitor cells appeared to differentiate into mast cell progenitors in the early stage of the culture, since less adherent cells (non mast cells) were detected in the cultures using inverted light microscopy. Using the instant protocol, the cells are kept for 14 days in hypoxia and 28 days in normoxia, a condition that allows sufficient time for the cells to be functionally mature at week 6. Cells start to show expression of both tryptase and chymase (maturation phenotypes of human connective tissue-type mast cells) at week 4. The addition of IL-4 to cultures in week 5 further promotes cell maturation. These cells start to respond to several stimuli (with histamine release and cytokine production/release) at week 6. Cells remain functionally responsive up to at least 20 weeks of culture.

TABLE 1

6-week protocol for culturing mast cells

| Time | $O_2$ conc. | Cytokines in Medium | Remarks |
| --- | --- | --- | --- |
| Day 0 | Hypoxia | SCF + IL-6 + IL-3 | CD34+ isolated from PBBC |
| Wk 1 | Hypoxia | SCF + IL-6 + IL-9 | Progenitor proliferation enhanced in presence of IL-9 and in hypoxic condition |
| Wk 2-3 | Normoxia | SCF + IL-6 | Transfer to normoxic condition to promote cell maturation |

TABLE 1-continued 6-week protocol for culturing mast cells

| Time | O₂ conc. | Cytokines in Medium | Remarks |
|---|---|---|---|
| Wk 4 | Normoxia | SCF + IL-6 | Cells start to show tryptase+ and/or chymase+ (by IHC) |
| Wk 5 | Normoxia | SCF + IL-6 + IL-4 | IL-4 included at late stage to further promote cell maturation |
| Wk 6 | Normoxia | Cell harvested | Cells start to show histamine release in response to several stimuli including IgE/anti-IgE |

1.c Cell Yield

Cells were harvested from the culture vessel at different time intervals and counted with a haematocytometer. The resultant cell number was plotted against time. Cell count was performed at regular time interval in order to monitor and maintain the seeding density at around $5 \times 10^5$ cells/ml as the cells were proliferating in the culture.

1.d Cell Morphology

Cells at week 4 and week 6 were washed once in PBS and cytospin onto a charged glass slide ($1 \times 10^4$ cells/slide). The cells were then fixed in Carnoy's fixative (60% ethanol, 30% chloroform, 10% glacial acetic acid) for 90 sec at room temperature. The slides were then rinsed in tap water and air dried. The slides can be stained immediately or kept at 4° C. for staining to be done subsequently. Mast cell morphology was observed under light microscope after Pappenheim's staining was performed. Briefly, the slides were rinsed in PBS for 5 min and then stained sequentially in 15% May-Grünwald's solution for 10 min, 7.5% May-Grüwald's solution for 20 min, and 5% Giemsa's solution for 30 min, all at room temperature. The slides were then rinsed in tap water, air dried and mounted with coverslips.

1.e Cell Function

These mast cells express both chymase and tryptase (see Example 2), thus resembling the phenotype of connective tissue-type mast cells. They also exhibit functional activation in response to (a) the stimulation by compound 48/80 and ionophores, and (b) the activation of various mast cell surface receptors, such as the high-affinity IgE receptors, the high-affinity IgG receptors, Toll-like receptors, and Substance P receptors. (see Example 3) Since these human mast cells can respond to the stimulation of compound 48/80 and the activation of Substance P receptors, our studies provide further evidence that these cells exhibit functional properties characteristic of connective tissue-type mast cells.

In a random sampling of 28 human buffy coats, 16 batches of human mast cell cultures that were generated from these 28 buffy coats after being cultured for 6 weeks using our culturing conditions exhibited 100% positive staining with both chymase and tryptase, suggesting that our protocol can achieve 100% cell purity in our mast cell culture preparations.

Example 2

Immunohistochemistry

Expression of tryptase and chymase in the cultured mast cells was visualized using DAKO cytomation LSAB2 System-HRP kit according to the manufacturer's instructions. Briefly, fixed cytospin slides were rinsed in distilled water. Endogenous peroxidase was quenched with hydrogen peroxide solution provided in the kit at room temperature for 5 min. The slides were then incubated with primary antibodies (1:1000 anti-tryptase, 1:1000 anti-chymase, both from Chemicon; or 1:1000 isotypic IgG control) at 4° C. overnight. The slides were then washed with TBS and incubated with biotinylated-link secondary antibody provided in the kit at room temperature for 30 min. Excess secondary antibody was washed away with TBS and the slides were incubated with streptavidin-HRP provided at room temperature for 30 min. Signals were developed with DAB substrate-chromogen solutions provided. The slides were then washed in water, counterstained with Mayer's hematoxylin, dehydrated with graded ethanol, cleared in xylene and mounted with coverslips. Results showed that these human mast cells generated in example 1 are stained positive for both chymase and tryptase.

Example 3

Assessment of Cell Functions

To validate that the human mast cell cultures are functionally responsive, the release of histamine, prostaglandin $D_2$ ($PGD_2$) and interleukin-8 (IL-8) in response to stimulations by anti-IgE, aggregated $IgG_1$, Toll-like receptor ligands, Substance P, compound 48/80 and ionophores was measured. The results suggest that such human mast cells generated in Example 1 exhibit functional properties of mature mast cells.

3.a Mast Cell Sensitization and Activation

Cultured mast cells at week 6, week 9 and week 12 were harvested, counted and seeded into 24-well plates in complete IMDM with 100 ng/ml SCF and 50 ng/ml IL-6.

IgE-dependent activation: Human mast cells were first sensitized by 0.5 µg/ml human myeloma IgE (Merck) in culture medium overnight. Unbound IgE was then removed by washing once with PBS. The cells were then resuspended in full HEPES buffer (FHB: 137 mM NaCl, 5.56 mM glucose, 12 mM HEPES, 2.7 mM KCl, 0.4 mM $NaH_2PO_4$ and 1 mM $CaCl_2$ at pH 7.4) supplemented with 0.03% human albumin (HA) (for release of histamine and $PGD_2$) or in IMDM with 10% FBS (for release of IL-8). The sensitized cells were challenged with anti-IgE (Sigma) (1 µg/ml) at 37° C. for 30 min for release of histamine and $PGD_2$, or with anti-IgE (0.25 µg/ml) overnight for release of IL-8.

IgG-dependent activation: Purified $IgG_1$ was purchased from Merck and aggregated IgG complexes were prepared by heating $IgG_1$ solution at 63° C. for 1 hour. Mature mast cells were incubated with 15 ng/ml human recombinant interferon-γ for 40 hours and then resuspended in FHB with 0.03% HA. The interferon-γ treated cells were stimulated with different concentrations of aggregated $IgG_1$ for 30 minutes for release of histamine.

3.b Histamine Release

Histamine released into the reaction buffer and the remaining granular histamine in the pellets were collected and analyzed by using Bran+Luebbe Autoanalyzer (AAIII Autoanalyzer, Bran+Luebbe, Germany) which chemically extracted histamine from the samples as described by Siraganian (Siraganian, R. P. 1974, *Analytical Biochemistry* 57(2): 383-394). The total amounts of histamine contained in these two fractions from the same experiment tube represent the total histamine content in the mast cells contained in that tube. For all stimulation studies, histamine released into the supernatant was expressed as a percentage of total cellular histamine content and all histamine release values were corrected for the spontaneous histamine release in buffer alone.

3.c $PGD_2$ Release

Human mast cells cultured for more than 6 weeks were first sensitized by 0.5 µg/ml human myeloma IgE (Merck) in culture medium overnight. Unbound IgE was then removed by washing once with PBS. The cells were then resuspended in full HEPES buffer (FHB: 137 mM NaCl, 5.56 mM glucose, 12 mM HEPES, 2.7 mM KCl, 0.4 mM $NaH_2PO_4$ and 1 mM $CaCl_2$ at pH 7.4) supplemented with 0.03% human albumin (HA), and then challenged by anti-human IgE or other stimuli (except $IgG_1$) for 30 min in a 37° C. water bath. The reaction was then stopped by adding ice-cold buffer and chilling on ice. Cell-free supernatant was collected following precipitation of cells by centrifugation at 4° C. $PGD_2$ release was measured by ELISA (Cayman) and presented as [pg/ml].

3.d IL-8 Release

Human mast cells cultured for more than 6 weeks were first sensitized by 0.5 µg/ml human myeloma IgE (Merck) in culture medium with 10% FBS overnight. IgE-sensitized mast cells were then washed in PBS to remove unbound IgE. The cells were resuspended in complete IMDM with 100 ng/ml SCF and 50 ng/ml IL-6 (with 10% FBS), and then challenged by anti-human IgE (Sigma) or other stimuli (except $IgG_1$) overnight at 37° C., 5% $CO_2$. Culture medium was harvested and cells were removed by centrifugation at 4° C. Amount of IL-8 released into the culture medium was measured by ELISA (BD).

Figure 5:
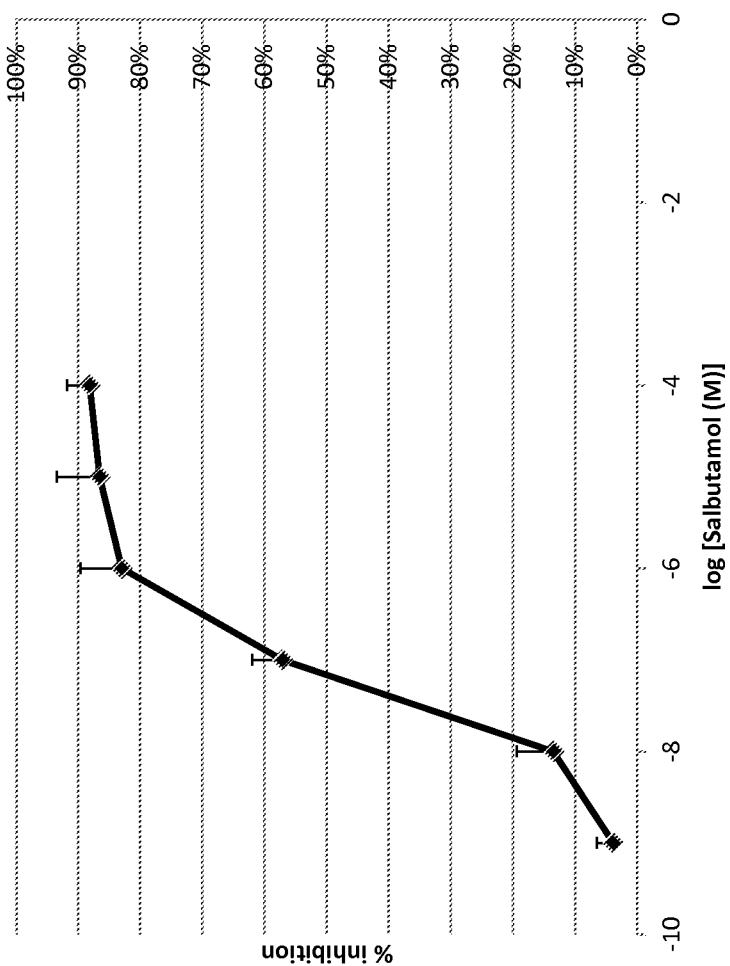
FIG. 5 shows inhibitory effect of Salbutamol on histamine release by human mast cell in response to anti-IgE according to one embodiment of the present invention.

Release of histamine, $PGD_2$ and IL-8 was observed in these mast cells generated in Example 1 in response to stimulations by anti-IgE, aggregated $IgG_1$, Toll-like receptor ligands, Substance P, compound 48/80 and ionophores (see FIGS. 1, 2, 3, 4). The IgE-dependent degranulation can be inhibited by incubating these cells with a β-adrenoceptor agonist, Salbutamol (see FIG. 5), or a Bruton's Tyrosine Kinase inhibitor. Therefore, this human mast cell culture system can be used as a surrogate for human tissue mast cells for screening and profiling pharmacological agents that inhibit mast cell functions.

Example 4

A Cell-Based Assay for Screening Tryptase Inhibitors

Primary human mast cells with functional phenotype of connective tissue-type mast cells were derived from peripheral blood using the protocol described in Example 1. Cells were stimulated via the high-affinity IgE receptors (FcERI) using an anti-IgE antibody and kept under various conditions (see conditions A to G below) for 6 hours and 16 hours. The supernatants were then collected and the MCP-1 level in the supernatants was determined.

The conditions used in the experiment are listed in Table 2 below.

TABLE 2

Treatment Conditions Employed in MCP-1 Studies

| Conditions | at 0 hour | at $6^{th}$ hour | at $22^{nd}$ hour |
|---|---|---|---|
| A | Anti-IgE | Frozen | / |
| B | Anti-IgE | Water | Harvest |
| C | Anti-IgE | 1X protease inhibitor cocktail | Harvest |
| D | Anti-IgE | APC366 | Harvest |
| E | Anti-IgE | Bestatin | Harvest |
| F | Anti-IgE | Chymostatin | Harvest |
| G | / | Anti-IgE | Harvest |

A: 6 hr reaction: sample was diluted at 6 hour and kept frozen at −80° C. (no further treatment);
B: Water control: sample was diluted at 6 hour and kept with water at 37° C. for 16 hours;
C: 1X protease inhibitor cocktail (Roche) treatment: samples were diluted at 6 hour and treated with Roche protease inhibitor cocktail for 37° C. for 16 hours;
D: APC366 (specific inhibitor of mast cell tryptase, Tocris Bioscience) treatment: sample was diluted at 6 hour and treated with APC366 at 37° C. for 16 hours;
E: Bestatin (specific inhibitor of metalloprotease, Sigma) treatment: sample was diluted at 6 hour and treated with Bestatin at 37° C. for 16 hours;
F: Chymostatin (specific inhibitor of chymotrypsin, Sigma) treatment: sample was diluted at 6 hour and treated with Chymostatin at 37° C. for 16 hours;
G: 16 hr reaction: sample was diluted at 16 hour and kept frozen at −80° C. (no further treatment).

Figure 6:
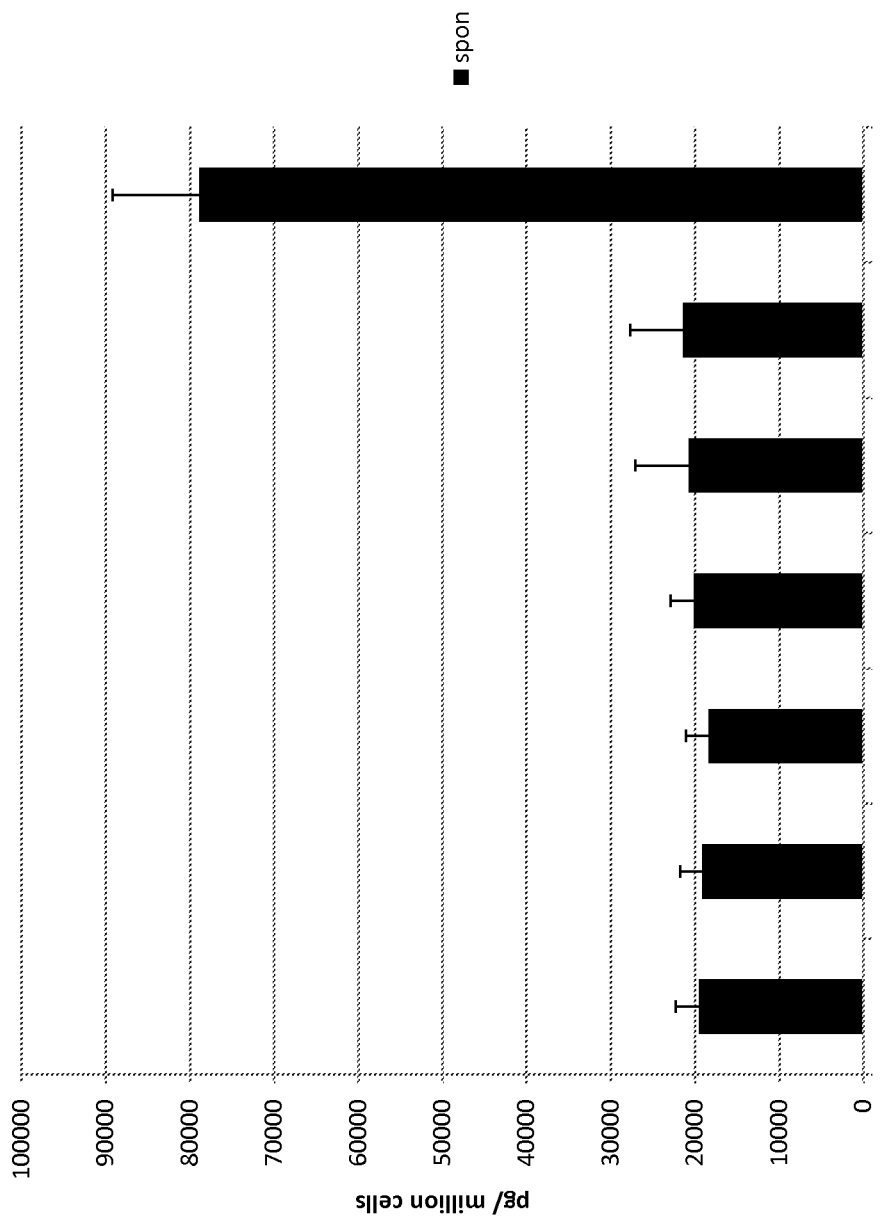
FIG. 6 shows the level of spontaneous release of MCP-1 by human mast cells according to one embodiment of the present invention.

The MCP-1 release profile of un-stimulated mast cells was investigated. FIG. 6 shows that un-stimulated mast cells release MCP-1 spontaneously in conditions A-G.

Figure 7:
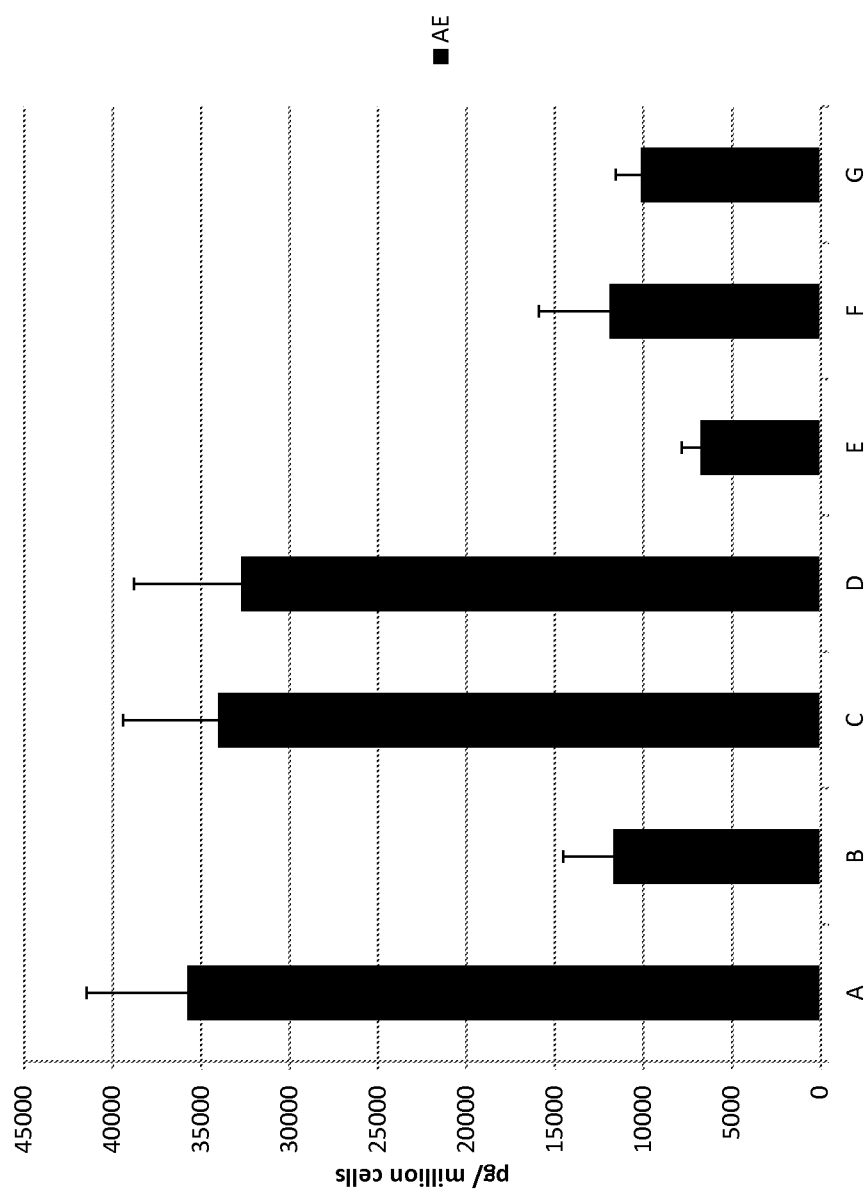
FIG. 7 shows the effects of different protease inhibitors on levels of MCP-1 secreted by stimulated human mast cells according to the same embodiment of the present invention.
Figure 9:
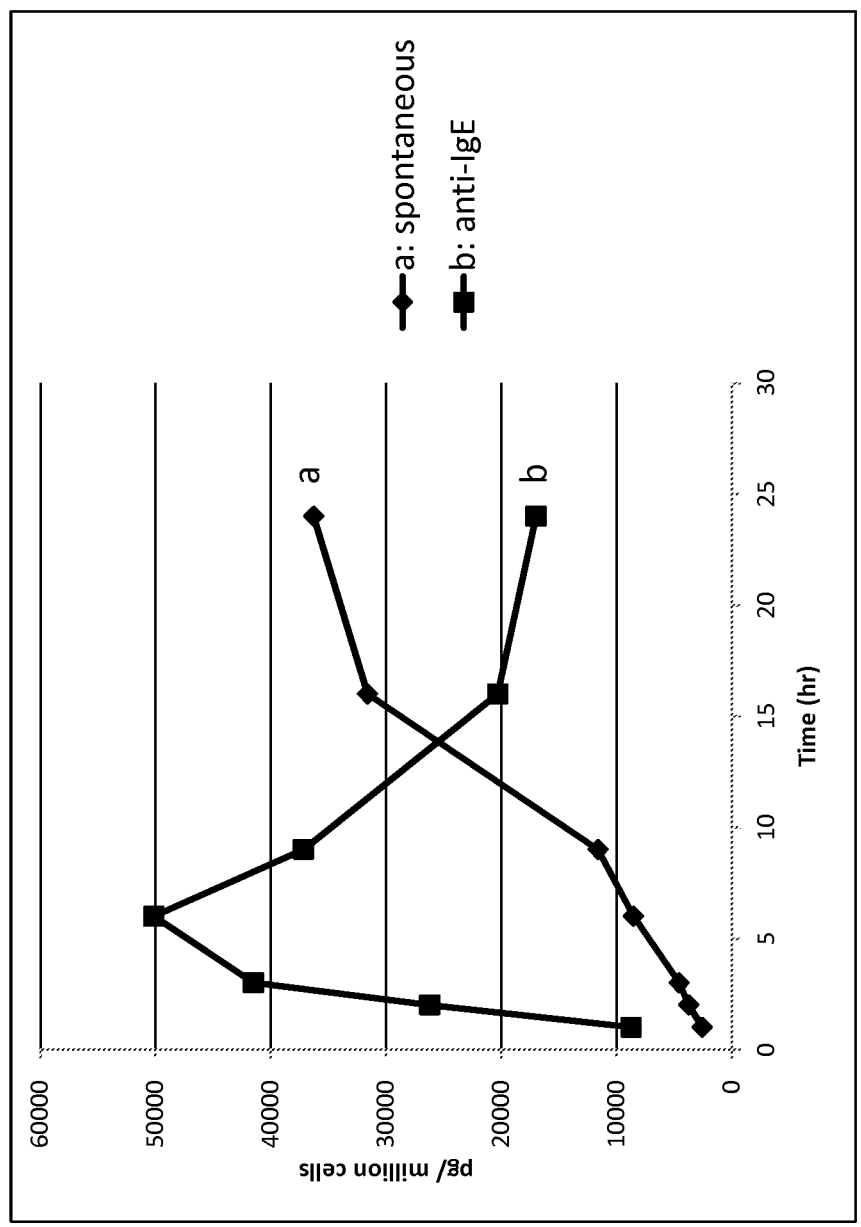
FIG. 9 shows the level of MCP-1 detected at different time points according to the same embodiment of the present invention.

The levels of MCP-1 released from activated mast cells were then measured in conditions A-G. FIG. 7 shows the amounts of MCP-1 detected in the reaction medium after the mast cells were stimulated by anti-IgE antibody for 6 hours and then incubated with protease inhibitors for another 16 hours. Upon stimulation with anti-IgE, levels of MCP-1 detected in the supernatants were significantly increased at 6 hours after stimulation and then decreased over a period of 18 hours (see FIG. 9). Based on this observation, regulation of mast cell functions can be assessed by measuring MCP-1 levels over a period of time covering the peak at the $6^{th}$ hour. For example, by monitoring MCP-1 levels resulting from stimulated mast cells from the $5^{th}$ hour to the $7^{th}$ hour, as the MCP-1 levels increase initially and then decrease, one can readily determine that these mast cells have been activated. These data also suggest the release of protease that degrades MCP-1 protein that is released from activated human mast cells.

The results shown in FIG. 7 demonstrate that incubation of the 6-hour reaction medium with either protease inhibitor cocktail or APC366, but not Bestatin and Chymostatin, can significantly inhibit the degradation of MCP-1 in the reaction medium by 90-95%, suggesting that tryptase is the protease that is released by these human connective tissue-type like mast cells generated in Example 1 upon stimulation via the high-affinity IgE receptors. The data implicate further that the release of MCP-1 and its degradation by the IgE-dependent release of tryptase from human connective-tissue like mast cells can be used as a novel cell-based assay approach for screening and profiling an agent with tryptase inhibitory activity. A skilled person would be able to understand that any agent with tryptase inhibitory activity can be screened and identified by measuring level of MCP-1 secreted by these mast cells over a period of time.

Figure 8:
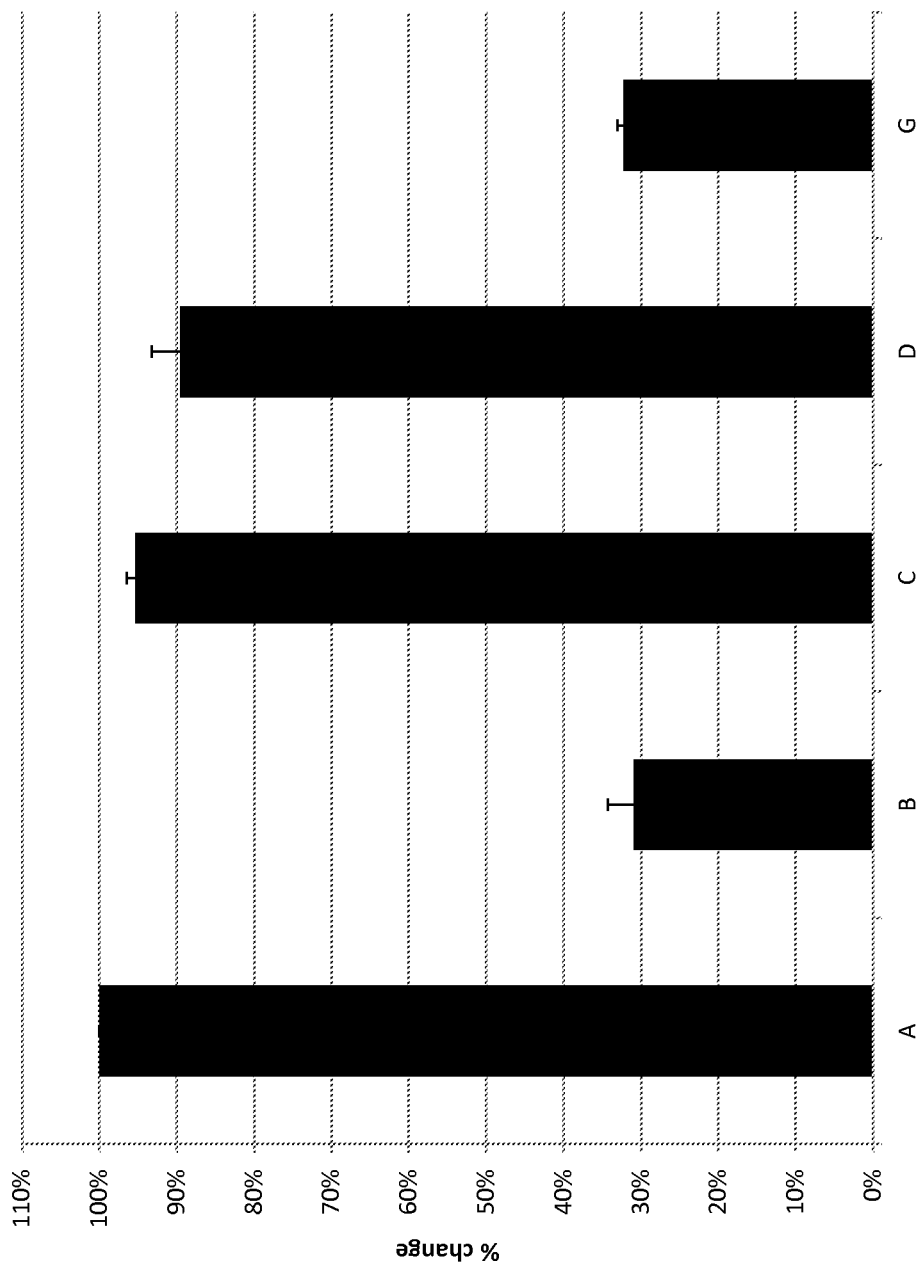
FIG. 8 shows the percentage change of MCP-1 levels at the 16$^{th}$ hour in various reaction mixtures relative to the MCP-1 level in the control at the 6th hour according to the same embodiment of the present invention.

The MCP-1 levels determined under conditions B, C, D and G, were plotted against the MCP-1 level for condition A, which exhibited peak MCP-1 level at the $6^{th}$ hour after stimulation. The results shown in FIG. 8 demonstrate that APC366 (a specific tryptase inhibitor) and protease inhibitor cocktail with tryptase inhibitory activity can inhibit MCP-1 degradation as the MCP-1 levels under conditions C and D are approximate the same as those under condition A. For the control groups B and G, significant degradation of MCP-1 was observed. These results show that the activated mast cells can secrete tryptase which degrades MCP-1 and that the inhibition of tryptase by tryptase inhibitors prevents the degradation of MCP-1.

Therefore, human mast cell cultures with functional phenotype of connective tissue-type mast cells can be used as a cell-based assay for assessing the tryptase inhibitory activity of an agent. If the agent possesses tryptase inhibitory activity, the levels of MCP-1 secreted by the activated mast cells and detected in the reaction medium are expected to remain unchanged for a period of time.

The exemplary embodiments of the present invention are thus fully described. Although the description referred to particular embodiments, it will be clear to one skilled in the art that the present invention may be practiced with variation of these specific details. Hence this invention should not be construed as limited to the embodiments set forth herein.

For instance, in Example 1, the human $CD34^+$ progenitor cells were kept under hypoxic condition for 2 weeks, but it is clear that other hypoxic time periods, e.g. 1.5-4 weeks, may be used according to the user's preference and depending on the rate of cell proliferation.

In Example 1, the culture was kept under normoxia condition for 4 weeks after being treated in hypoxic condition for 2 weeks, but it is clear that other normoxic time periods, e.g. 3-6 weeks, may be used according to the user's preference and the rate of cell maturation.

Further in Example 1, cells were cultured in a medium with 1 ng/ml IL-3, but it is clear that other concentrations of IL-3 may be used, such as 0.1-4 ng/ml. Cells were cultured in a medium with 15 ng/ml IL-9, but it is clear that other concentrations of IL-9 may be used, such as 1-50 ng/ml. Cells were cultured in a medium with 200 ng/ml SCF, but it is clear that other concentration of SCF may be used, such as 100-500 ng/ml. Cells were cultured in a medium with 100 ng/ml IL-6, but it is clear that other concentration of IL-6 may be used, such as 50-500 ng/ml. Cells were cultured in a medium with 10 ng/ml IL-4, but it is clear that other concentration of IL-4 may be used, such as 1-100 ng/ml.

$CD34^+$ progenitor cells were described as being obtained from human peripheral blood buffy coat, but it is clear that $CD34^+$ progenitor cells may be obtained by various conventional methods in the art. Anti-IgE is used to stimulate mast cells as described herein, but it is clear that other stimuli may be used, such as aggregated $IgG_1$.

Example 4 shows that APC366 and protease inhibitor cocktail can inhibit MCP-1 degradation through their abilities to inhibit the activity of mast cell-secreted tryptase. Therefore, it is obvious for one skilled in the art to expect that other agents with tryptase inhibitory activity can also inhibit MCP-1 degradation, and thus such agents can be screened and identified by measuring levels of MCP-1 secreted by such human mast cells.

We claim:

1. A method to make a mast cell culture comprising steps of (a) treating $CD34^+$ progenitor cells under hypoxic condition for 1 week in a medium comprising SCF, IL-6 and IL-3 to generate an initial-stage cell culture; (b) treating the initial-stage cell culture under hypoxic condition for 0.5-2.5 weeks in a medium comprising SCF, IL-6 and IL-9 to form an intermediate-stage cell culture; (c) treating the intermediate-stage cell culture under normoxic condition for 2.5-3.5 weeks in a medium comprising SCF and IL-6 to generate an immature mast cell culture, wherein a concentration of IL-3 in the medium in step (a) is 0.1-4 ng/ml, a concentration of IL-6 in the media in steps (a), (b) and (c) is 50-500 ng/ml, and a concentration of IL-9 in the medium in step (b) is 1-50 ng/ml; and (d) treating the immature mast cell under normoxic condition in a medium comprising SCF, IL-6 and IL-4, wherein a concentration of IL-6 in the medium in step (d) is 50-500 ng/ml, a concentration of IL-4 in the medium in step (d) is 1-100 ng/ml and a concentration of SCF in the media in steps (a), (b), (c), and (d) is 100-500 ng/ml.

2. The method of claim 1, wherein the concentration of SCF is 200 ng/ml.

3. The method of claim 1, wherein the concentration of IL-6 is 100 ng/ml in steps (a), (b) and (c).

4. The method of claim 1, wherein the concentration of IL-4 in the medium in step (d) is 10 ng/ml.

5. The method of claim 1, wherein the $CD34^+$ progenitor cells are human $CD34^+$ progenitor cells.

6. The method of claim 1, wherein the initial-stage cell culture is treated under hypoxic condition for 1 week in step (b).

7. The method of claim 1, wherein the intermediate-stage cell culture is treated under normoxic condition for 3 weeks in step (c).

8. The method of claim 1, wherein the concentration of IL-3 in the medium in step (a) is 1 ng/ml.

9. The method of claim 1, wherein the concentration of IL-9 in the medium in step (b) is 15 ng/ml.

10. The method of claim 1, wherein the concentration of IL-6 is 100 ng/ml in step (d).

* * * * *